| (12) | United States Patent | (10) Patent No.: US 10,245,079 B2 |
|---|---|---|
| | Sournac et al. | (45) Date of Patent: Apr. 2, 2019 |

(54) VERTEBRAL OSTEOSYNTHESIS EQUIPMENT

(71) Applicant: MEDICREA INTERNATIONAL, Rillieux-la-Pape (FR)

(72) Inventors: Denys Sournac, Reyrieux (FR); Thomas Mosnier, Anthon (FR)

(*) Notice: Subject to any disclaimer, the term of this patent is extended or adjusted under 35 U.S.C. 154(b) by 0 days.

(21) Appl. No.: 15/564,714

(22) PCT Filed: Apr. 14, 2016

(86) PCT No.: PCT/IB2016/052126
§ 371 (c)(1),
(2) Date: Oct. 5, 2017

(87) PCT Pub. No.: WO2016/174538
PCT Pub. Date: Nov. 3, 2016

(65) Prior Publication Data
US 2018/0110546 A1      Apr. 26, 2018

(30) Foreign Application Priority Data

Apr. 29, 2015   (FR) ..................................... 15 53858

(51) Int. Cl.
  *A61B 17/70*   (2006.01)
(52) U.S. Cl.
  CPC ...... *A61B 17/7041* (2013.01); *A61B 17/7053* (2013.01); *A61B 17/7037* (2013.01)
(58) Field of Classification Search
  CPC ............ A61B 17/7041; A61B 17/7053; A61B 17/7037

(Continued)

(56) References Cited

U.S. PATENT DOCUMENTS 8,636,770 B2 *  1/2014  Hestad ............... A61B 17/7032
                                                           606/248
9,314,275 B2    4/2016  Clement et al.
(Continued)

FOREIGN PATENT DOCUMENTS

EP    2279707 A1    2/2011
FR    2976783 A1   12/2012

OTHER PUBLICATIONS

International Search Report of the ISA—EPO, dated Jun. 17, 2016.

*Primary Examiner* — Pedro Philogene
*Assistant Examiner* — David C Comstock
(74) *Attorney, Agent, or Firm* — Patshegen IP LLC; Moshe Pinchas

(57) ABSTRACT

This equipment (1) comprises at least one connecting bar (100), at least one flexible ligament (101) and at least one connecting assembly (1). According to the invention, —a connecting part (2) of said assembly forms an engagement conduit (15) for engagement of the connecting bar (100); —the body (6) of this part (2) has a central conduit (10) for receiving a tightening part (3) and two lateral conduits (11) for receiving the strands of the ligament; —said tightening part (3) comprises a threaded pin (16) capable to be engaged into said central conduit (10) and a base (17) for bearing against the connecting bar (100); —the nut (4) has a distal portion (31) coaxial with itself, on which is pivotally mounted a pressing ring (5) adapted to be engaged into said lateral conduits (11) and to tighten the strand of the ligament (101).

7 Claims, 3 Drawing Sheets

(58) Field of Classification Search
USPC .................................... 606/250, 251, 263
See application file for complete search history.

(56) References Cited

U.S. PATENT DOCUMENTS

| | | | |
|---|---|---|---|
| 2009/0248082 A1* | 10/2009 | Crook ................ | A61B 17/7064 606/263 |
| 2009/0292317 A1* | 11/2009 | Belliard ............. | A61B 17/7053 606/263 |
| 2013/0150892 A1* | 6/2013 | Douget .............. | A61B 17/7032 606/263 |
| 2013/0261668 A1* | 10/2013 | Douget .............. | A61B 17/7032 606/278 |
| 2014/0257401 A1 | 9/2014 | George et al. | |
| 2016/0249957 A1* | 9/2016 | Deneuvillers ...... | A61B 17/7049 606/263 |

* cited by examiner

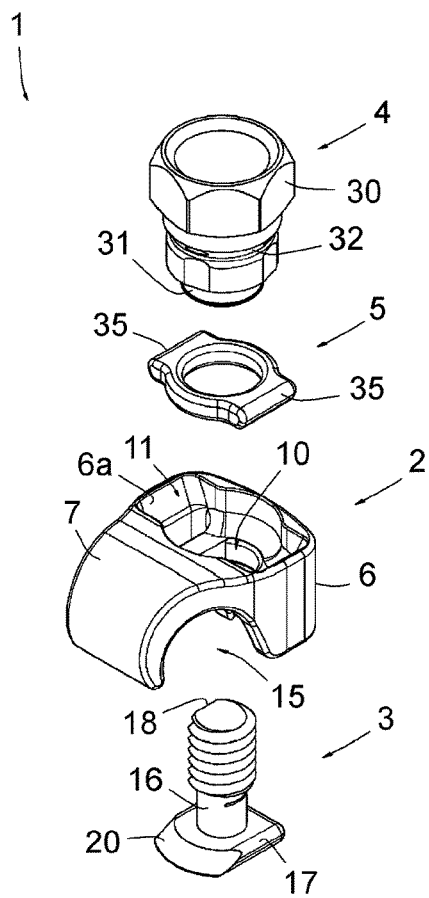
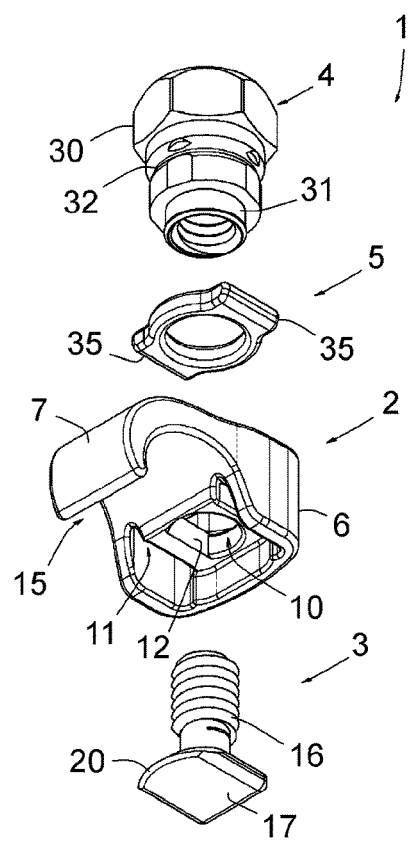
FIG. 1
FIG. 2
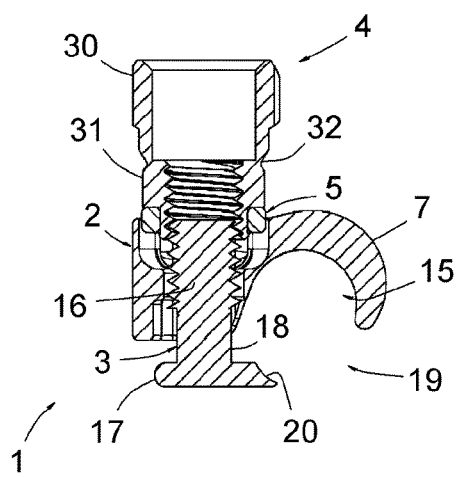
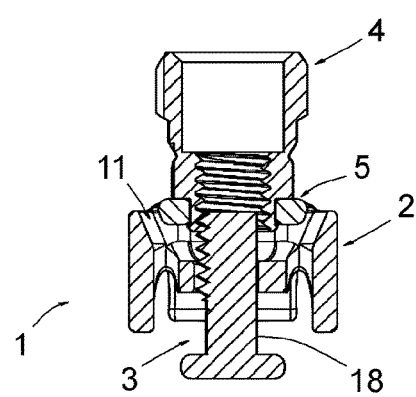
FIG. 3
FIG. 4

VERTEBRAL OSTEOSYNTHESIS EQUIPMENT

The present invention relates to a vertebral osteosynthesis equipment.

In order to treat degeneration of one or several vertebral joints, the use of vertebral osteosynthesis equipment is well known comprising connecting bars intended to connect together several vertebrae to be treated, anchoring members giving the possibility of attaching these rods to the vertebrae, and connecting assemblies allowing connection of the anchoring members to the connecting bars.

In a type of equipment, the anchoring members are formed with flexible ligaments engaged around the laminae of the vertebrae to be treated, the strands of which are engaged and blocked through respective connecting assemblies. The publication of French patent application No. FR 2 976 783, in the name of the Applicant, illustrates an equipment of this type.

The equipment according to this prior document globally gives satisfaction but may however be improved. Indeed, a connecting assembly which this equipment comprises has a relatively voluminous connecting part which may be a problem for treating certain portions of a vertebral column, notably thorax vertebrae, because the connecting parts of the different connecting assemblies of an assembly may be sensitive under the skin of the patient. Further, the known structure of this connecting part imposes that the connecting parts be engaged on a same connecting bar through the end of this rod, which is certainly a practical constraint. Indeed, the rods have to be curved along the desired correction of the position of the vertebrae, and it is seldom that the first achieved curvature is perfect; the correction of the curvature of the rod is accomplished by a process of trial and error, which imposes several settings into place and successive withdrawals of the rod. This constraint of use complexifies and notably prolongs the surgical intervention. A connecting assembly according to the prior equipment also implies the tightening of two screws upon its setting into place, one for immobilizing said connecting part with respect to the connecting bar and the other one for immobilizing this connecting part with respect to the ligament, which contributes to complexifying and prolonging the surgical intervention. Further, the two strands of a ligament, returning to the corresponding connecting part after having engaged the ligament around the lamina of the vertebra, has to be twisted over a quarter of a turn so as to be capable to be engaged into this part; this twisting is not desirable as regards the mechanical strength of the ligament and the resistance of this ligament to wear, and contributes to raising the connecting part with respect to the corresponding vertebra, and therefore to the risk of making the equipment sensitive under the skin of the patient.

The present invention has the goal of providing a vertebral osteosynthesis equipment providing a remedy to the whole of the aforementioned drawbacks.

The publications of patent applications No. US 2014/257401 A1 and EP 2 279 707 A1 describe equipment which do not give the possibility of finding a remedy to the whole of these drawbacks.

The equipment according to the invention comprises:
at least one connecting bar having a length such that it is capable to span several vertebrae to be treated, having a general longitudinal direction;
at least one flexible ligament adapted to be engaged onto a vertebra to be treated, and
at least one assembly for connecting the ligament to the connecting bar, comprising:
a connecting part which has a body forming a conduit for engagement of the ligament and which has a conduit for engagement of the connecting bar;
a nut for tightening the ligament in the corresponding conduit; and
means for tightening the connecting bar in the corresponding conduit;
the connecting part has a curved portion connected to the body, which interiorly delimits the engagement conduit for the connecting bar and which partly surrounds this connecting bar when the latter is placed in this conduit;
the body has a central conduit and two lateral conduits; the central conduit receives a tightening part forming said means for tightening the connecting bar in the corresponding conduit;
the body has means for blocking this tightening part in rotation relatively to it; both lateral conduits are located on either side of the central conduit, in locations distant from each other; each lateral conduit has a proximal portion which communicates with the central conduit and which, on a radially external side, is delimited by a wall of the body which is tilted relatively to the axis of the central conduit, this tilt being such that a distal area of this wall is closer to the axis of the central conduit than a proximal area of this wall;
said tightening part comprises a threaded pin and a base, and comprises means for its blocking in rotation with respect to the body; the threaded pin is capable to be engaged into said central conduit and to receive the nut by screwing; the screwing or unscrewing of this nut relatively to the threaded pin allows the tightening part to either adopt a clamping position, or an untightening position; said base extends in a plane perpendicular to the axis of the pin, over a distance such that it is able, in said tightening position, of bearing against the connecting bar when the connecting bar is engaged into said engagement conduit; in said untightening position, this base delimits, with the curved portion, a passage for engaging the connecting bar into said conduit along a direction transverse to the general longitudinal direction of this bar and does not form an obstacle for this engagement;
the nut has a distal portion coaxial with itself, on which is pivotally mounted a pressing ring adapted to be engaged into said lateral conduits; in said loosening position, the pressing ring is found at a distance from said corresponding tilted wall such that a strand of the ligament is capable to be engaged into the space located between this pressing ring and this tilted wall; in said tightening position, the pressing ring is found at a distance from said corresponding tilted wall such that it tightens the strand of the ligament between itself and this tilted wall, immobilizing this strand relatively to the connecting part.

It will be understood that the terms of "proximal" and "distal" are to be considered with respect to the connecting assembly as it is found in its implantation position, "proximal" referring to a position closer to the practitioner and "distal" to a position further away from this practitioner.

Thus it appears that according to the invention single tightening means are provided, formed by said tightening part and the nut, so as to allow the connecting bar to be tightened in the engagement conduit and the strands of the ligament to be tightened in said lateral conduits. In addition to the simplification and acceleration of the setting into place of the equipment which results therefrom, this structure gives the possibility, jointly with the fact that said engagement conduit is open for allowing transverse insertion of this rod, of obtaining a not very voluminous connecting part, reducing very notably the risk that the connecting parts of an assembly be sensitive under the skin of the patient. A connecting bar may be transversely engaged onto the various connecting parts of this assembly, which greatly facilitates the settings into place and successive withdrawals of the rod during successive operations for bending this rod.

Preferably, the lateral conduits are diametrically opposite to each other, while being aligned along a direction parallel to the axis of the engagement conduit for engaging the connecting bar.

Thus, both strands of the ligament are not twisted over a quarter of a turn when they return to the corresponding connecting part after having engaged the ligament around the lamina of the vertebra, which suppresses any undesirable twisting of the strands and contributes to lowering the connecting part with respect to the corresponding vertebra, and therefore to reducing the risk of making the equipment sensitive under the skin of the patient.

Preferably, the body of the connecting part comprises, in each lateral conduit, at least one anti-return protrusion forming a pronounced edge, this anti-return protrusion allowing sliding of a strand of the ligament in this conduit in the distal-proximal direction, with friction, and opposing, by penetration of said edge into the material of the ligament, the sliding of the strand in the opposite direction.

This protrusion thus gives the possibility of maintaining the strand under tension in the conduit for the time during which the nut is maneuvered so as to bring the pressing ring to achieve the definitive blocking of the strand of the ligament. This maintaining greatly facilitates the setting into place of the equipment.

Said base of the tightening part may notably extend, in a projection along the axis of the screwing of the nut on the threaded pin, over about one quarter of the diameter of the engagement conduit for engaging the connecting bar.

This base advantageously comprises a rounded machined area at its area intended to come into contact with the connecting bar, giving the possibility of increasing the surface area through which this base comes into contact with the connecting bar.

Said means for blocking the tightening part in rotation with respect to the body are preferably formed by a flat made on this body at the central conduit and by a corresponding flat made on the threaded pin which the tightening part comprises.

Preferably, each aforementioned tilted wall is laterally bordered by two walls perpendicular to it, and the pressing ring has two radial extensions, one of which is capable to be engaged into the proximal portion of a lateral conduit in which are found said tilted wall and said perpendicular walls, and the other one of which is capable to be engaged into the proximal portion of the other lateral conduit in which are found said tilted wall and said perpendicular walls.

Thus, the engagement of said extensions between said perpendicular walls gives the possibility of blocking the pressing ring in rotation with respect to the connecting part, so that the strands of the ligament are tightened by pure axial translation of the pressing ring. These arrangements suppress a risk of pivoting of the ring with respect to the strands at the end of the tightening, which would be capable to damage the material of the ligament.

The invention will be well understood, and other features and advantages thereof will become apparent, with reference to the appended schematic drawing, illustrating, as a non-limiting example, a preferred embodiment of a connecting assembly which the relevant equipment comprises.

FIG. 1 is an exploded perspective top view thereof;

FIG. 2 is a view similar to FIG. 1 thereof, from the bottom;

FIG. 3 is a sectional view thereof passing through the axis of a nut which it comprises, and along a plane perpendicular to the axis of a conduit for receiving a connecting bar, which it forms, the connecting assembly being illustrated in an untightened position of such a connecting bar;

FIG. 4 is a view thereof similar to FIG. 3, as a sectional view passing through the axis of the nut and along a plane parallel to the axis of the receiving conduit;

FIGS. 1 and 2 illustrate a connecting assembly 1 which is part of the vertebral osteosynthesis equipment.

Figure 5:
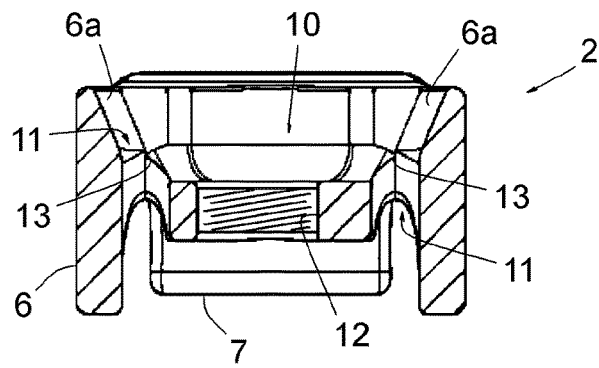
FIG. 5 is a view of a connecting part which it comprises, in a section view identical with that of FIG. 4 and at an enlarged scale.
Figure 6:
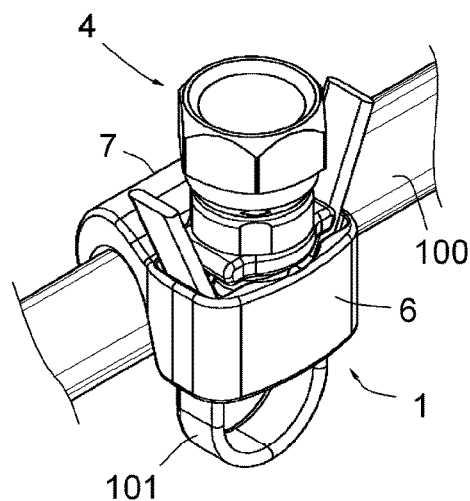
FIG. 6 is a perspective view of the connecting assembly, with engagement of the connecting bar into the receiving conduit and engagement of a ligament through the body of the connecting part.
Figure 7:
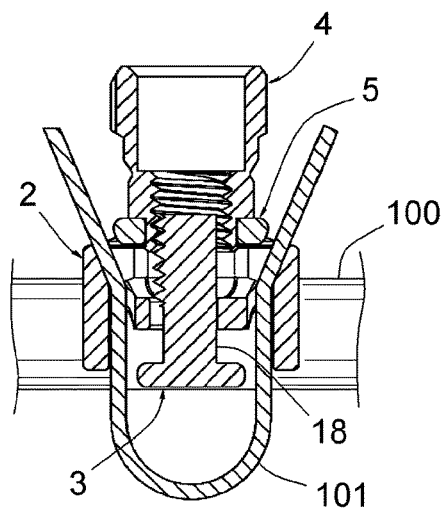
FIG. 7 is a view thereof, similar to FIG. 6, according to a sectional view similar to FIG. 4, in a partial tightening position of the connecting bar in said engagement conduit and in a non-tightening position of the ligament.
Figure 8:
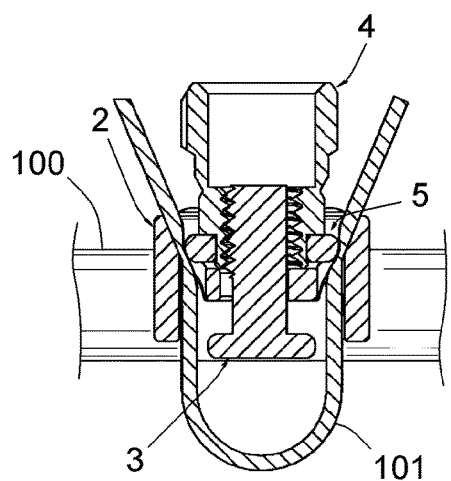
FIG. 8 is a view thereof similar to FIG. 7, in a position for tightening the connecting bar in said engagement conduit and for tightening the ligament in said body.
Figure 9:
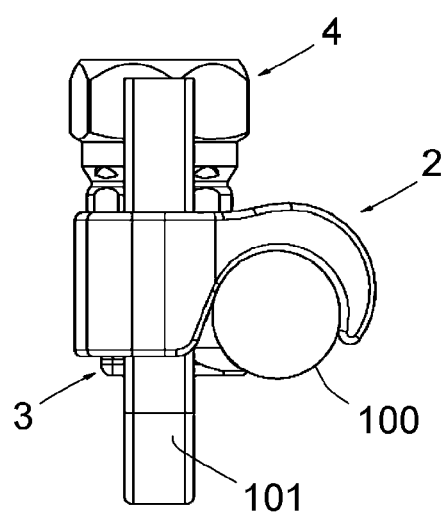
FIG. 9 is a side view thereof, in this same tightening position.

This equipment, well known per se, comprises connecting bars 100, one of which is visible in FIGS. 6 to 9, intended to connect between them several vertebrae to be treated, flexible ligaments 101, one of which is visible on these same FIGS. 6 to 9, intended to be engaged around the laminae of the vertebrae to be treated, and a series of connecting assemblies 1 intended to be crossed by the strands of the ligaments 101 so as to connect these ligaments, and therefore the vertebrae to the connecting bars 100.

Each connecting assembly 1 comprises a connecting part 2, a tightening part 3, a nut 4 and a pressing ring 5.

The connecting part 2 has a body 6 and a curved portion 7 connected to this body.

As more particularly visible in FIG. 5, the body 6 has a central conduit 10 and two lateral conduits 11.

The central conduit 10 is intended to receive a threaded pin 16 which the tightening part 3 forms. It has a flat 12 giving the possibility of blocking this pin, and therefore the tightening part 3, with respect to the body 6.

Both lateral conduits 11 are located on either side of the central conduit 10, and are intended to receive both strands of the ligament 101 when these strands return to the connecting part 2 after having engaged the ligament around the lamina of a vertebra.

The lateral conduits 11 are diametrically opposite to each other, while being aligned along a direction parallel to the axis of an engagement conduit 15 of the connecting bar 100, which the curved portion 7 forms. Each of them has a distal portion which is separate from the central conduit 10 and a proximal portion which communicates with this central conduit; on a radially external side, this proximal portion of each lateral conduit 11 is delimited by a wall 6a of the body 6 which is tilted with respect to the axis of the central conduit 10, this tilt being such that a distal area of this wall 6a is closer to the axis of the central conduit 10 than a proximal area of this wall 6a. Each wall 6a is laterally bordered by two walls perpendicular to it.

The body 6 also comprises, in each lateral conduit 11, an anti-return protrusion 13 forming a pronounced edge, visible in FIG. 5. This protrusion 13 allows sliding of a strand of the ligament 101 in this conduit 11 in the distal-proximal direction (therefore from bottom to top in this FIG. 5), with friction, and opposes by penetration of said edge into the material of the ligament 101, to the sliding of the strand in the opposite direction.

The curved portion 7 is connected to the body 6, with which it forms a single and same part. It interiorly delimits the aforementioned engagement conduit 15 and is capable to partly surround the connecting bar 100 when the latter is placed in this conduit, see FIG. 9.

The tightening part 3 comprises the aforementioned threaded pin 16 and a base 17 integral with this pin.

The latter is intended to be engaged into the central conduit 10 and then to receive the nut 4 by screwing on its proximal end. It has a flat 18 capable to cooperate with the flat 12 of the body 6, so that the tightening part 3 is blocked in rotation with respect to the body 6 during screwing or unscrewing of the nut 4. As this is visible by comparison of FIGS. 3 and 4 with FIGS. 8 and 9, the screwing of this nut 4 on the pin 16 gives the possibility to the tightening part 3 of adopting a tightening position (visible in FIGS. 8 and 9), and the unscrewing of this nut 4 with respect to the pin 16 allows the tightening part 3 to adopt an untightening position (visible in FIGS. 3 and 4).

The base 17 extends in a plane perpendicular to the axis of the pin 16, and has a dimension, along this plane, ensuring that it extends, in a projection along the axis for screwing the nut 4 on the pin 16, over about one quarter of the diameter of the conduit 15, as visible in FIG. 3. In FIGS. 3 and 4 it appears that, in the untightening position, the base 17 delimits, with the curved portion 7, a passage 19 for engaging the rod 100 into the conduit 15 along a direction transverse to the general longitudinal direction of this rod, and that the base 17, in this position, is not an obstacle to this engagement. In the tightening position, see FIGS. 8 and 9, the base 17 bears against the rod 100 engaged into the conduit 15, thus closing the passage 19 and immobilizing this rod in this conduit. The base 17 for this purpose has a rounded machined area 20 at its area intended to come into contact with the rod 100, giving the possibility of increasing its contact surface area with this rod.

The nut 4 has a proximal gripping portion 30, with six edges, a distal portion 31, coaxial with itself, of a circular shape, on which is pivotally mounted the pressing ring 5, and a circular area of reduced thickness 32, intended to be broken at the end of screwing so as to give the possibility of separating the gripping portion 30 from the distal portion 31. The mounting of the ring 5 on the distal portion 31 is notably achieved by snapping-on the ring beyond a bulge made on the distal end of the extension 30, or by slightly crimping this distal end on this ring 5.

The ring 5 has two extensions 35 capable to be engaged into the proximal portions of the lateral conduits 11. In said untightening position, each extension 35 is engaged into such a corresponding proximal portion and is found at a distance from said tilted wall 6a which is such that a strand of the ligament 101 is capable to be engaged into the space located between this extension 35 and this wall 6a, see FIG. 4; during the screwing of the nut, the base 17 comes into contact with the rod 100, immobilizing the rod 100 in the conduit 15, and the extensions 35 come into contact with the strands of the ligament 101; in the partial tightening position visible in FIG. 7, the strands of the ligament are not tightened, so that the ligament 101 may be tensioned; continuation of the tightening of the nut 4 gives the possibility of bringing the connecting assembly 1 into the tightening position visible in FIG. 8; the tightening part 3 being immobilized with respect to the body 6 by the base 17 coming into contact with the rod 100, each extension 35 is caused to tighten the strand of the ligament 101 between it and the tilted wall 6a, immobilizing this strand with respect to the connecting part 2.

Thus it appears that the invention provides a connecting assembly 1 comprising exclusive tightening means, formed by the tightening part 3 and the nut 4, which give the possibility of both tightening the rod 100 in the conduit 15 and the strands of the ligament 101 in said lateral conduits 11. In addition to the simplification and acceleration of the implantation of the equipment, this structure gives the possibility, jointly with the fact that the conduit 15 is opened for allowing transverse insertion of the rod 100, of obtaining a not very voluminous connecting part 2, reducing more notably the risk that the connecting parts 2 of a same assembly are sensitive under the skin of the patient. A rod 100 may further be engaged transversely on the different connecting parts 2 of the assembly, which greatly facilitates the settings into place and successive withdrawals of the rod(s) 100 during successive operations for bending this or these rods.

The fact that the lateral conduits 11 are aligned along a direction parallel to the axis of the conduit 15 gives the possibility that both strands of a ligament 101 are not twisted over a quarter of the turn when they return to the corresponding connecting part 2 after having engaged the ligament around the lamina of the vertebra, as visible in FIGS. 6 to 9. An undesirable twisting of these strands is thus suppressed, which contributes to lowering the connecting part 2 with respect to the corresponding vertebra, and therefore to reduce the risk of making the equipment sensitive under the skin of the patient.

Therefore, the equipment according to the invention has determining advantages as compared with homologous equipment according to the prior art and finds a remedy to the drawbacks of these equipment.

The invention claimed is:

1. A vertebral osteosynthesis equipment, wherein the equipment comprises:
   at least one connecting bar having a length such that it is capable to span several vertebrae to be treated, having a general longitudinal direction;
   at least one flexible ligament adapted to be engaged onto a vertebra to be treated, and
   at least one assembly for connecting the ligament to the connecting bar, comprising:
   a connecting part having a curved portion defining an engagement conduit for engagement of the connecting bar said curved portion partly surrounds the connecting bar when the latter is placed in the engagement conduit; the connecting part further includes a central conduit and two lateral conduits each located on one side of the central conduit, in locations distant from each other, each said lateral conduit is configured for holding a strand of the ligament and each said lateral conduit is defined between the central conduit and a radially external wall of the connecting part, said external wall having an inner tilted portion which is tilted outwardly with respect to an axis of said central conduit;

a nut having an inner threaded wall;

a tightening part having a threaded pin configured for engaging said threaded wall of said nut through said central conduit, and a base extending in a plane transversely to an axis of the threaded pin, said base being configured for tightening the connecting bar in the engagement conduit; and a pressing ring mounted on said nut and being configured to engage said tilted portion of each of said lateral conduits;

wherein the central conduit is configured for blocking the tightening part in rotation relatively to the central conduit;

wherein said tightening part and said nut are configured such that when the nut is screwed relative to the threaded pin through the central conduit said base engages the connecting bar when the connecting bar is disposed inside said engagement conduit; and the pressing ring urges the strand of the ligament towards the tilted wall, securing the strand relatively to the connecting part.

2. The vertebral osteosynthesis equipment according to claim 1, wherein the lateral conduits are diametrically opposite to each other, while being aligned along a direction parallel to the axis of the engagement conduit for engaging the connecting bar.

3. The vertebral osteosynthesis equipment according to claim 1, wherein body of the connecting part comprises, in each lateral conduit, at least one anti-return protrusion forming a pronounced edge, this anti-return protrusion allowing sliding of a strand of the ligament in this conduit in the distal-proximal direction, with friction, and opposing, by penetration of said edge into the material of the ligament, the sliding of the strand in the opposite direction.

4. The vertebral osteosynthesis equipment according to claim 1, wherein said base of the tightening part extends, in a projection along the axis of the screwing of the nut on the threaded pin, over about one quarter of the diameter of the engagement conduit for engaging the connecting bar.

5. The vertebral osteosynthesis equipment according to claim 1, wherein said base comprises a rounded machined area at its area intended to come into contact with the connecting bar.

6. The vertebral osteosynthesis equipment according to claim 1, wherein said central conduit includes a flat made on an inner surface of the central conduit and the threaded pin includes a corresponding flat configured to block the rotation of the tightening part with respect to the central conduit.

7. The vertebral osteosynthesis equipment according to claim 1, wherein:

each aforementioned tilted wall is laterally bordered by two walls perpendicular to it, and the pressing ring has two radial extensions, one of which is capable to be engaged into the proximal portion of a lateral conduit in which are found said tilted wall and said perpendicular walls, and the other one of which is capable to be engaged into the proximal portion of the other lateral conduit in which are found said tilted wall and said perpendicular walls.

* * * * *